United States Patent [19]

Junino et al.

[11] Patent Number: 4,865,618
[45] Date of Patent: Sep. 12, 1989

[54] NEW CHLORO-META-PHENYLENEDIAMINES, THEIR USE AS COUPLERS IN THE OXIDATION DYEING OF KERATINOUS FIBRES, DYEING COMPOSITIONS FOR HAIR CONTAINING THESE COMPOUNDS AND DYEING PROCESS USING THE SAID

[75] Inventors: Alex Junino, Livry-Gargan; Jean J. Vandenbossche, Aulnay-sous-Bois; Herve Borowiak, Tremblay-les-Gonesse; Gerard Lang, Saint-Gratien, all of France

[73] Assignee: L'Oreal, Paris, France

[21] Appl. No.: 200,399

[22] Filed: May 31, 1988

[30] Foreign Application Priority Data

May 29, 1987 [LU] Luxembourg .............................. 86904

[51] Int. Cl.⁴ ..................... A61K 7/13; C07C 91/40; C07C 91/42; C07C 87/60
[52] U.S. Cl. ............................................. 8/411; 8/408; 8/416; 8/421; 564/430; 564/442; 564/443
[58] Field of Search .................... 564/442, 443; 8/408, 8/411, 416, 421

[56] References Cited

U.S. PATENT DOCUMENTS 4,566,876  1/1986  Brown et al. .......................... 8/411

FOREIGN PATENT DOCUMENTS 0075242  3/1983  European Pat. Off. .

OTHER PUBLICATIONS

Chemical Abstracts, vol. 64, No. 13, Jun. 20, 1966, Col. 19553a–c, Kametani et al.

*Primary Examiner*—Paul Lieberman
*Assistant Examiner*—John F. McNally
*Attorney, Agent, or Firm*—Cushman, Darby & Cushman

[57] ABSTRACT

New chloro-meta-phenylenediamines, their use as couplers in the oxidation dyeing of keratinous fibres, dyeing compositions for hair containing these compounds and dyeing process using the said compositions.

The invention relates to the compounds of formula:

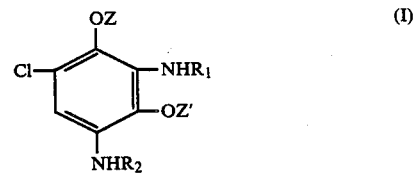

(I)

in which Z and Z' denote, independently of one another, an alkyl radical having from 1 to 4 carbon atoms or a hydroxyalkyl radical having from 2 to 4 carbon atoms, and $R_1$ and $R_2$ denote, independently of one another, a hydrogen atom, an alkyl radical having from 1 to 4 carbon atoms or a mono- or polyhydroxyalkyl radical having 2 or 3 carbon atoms, to their addition salts with an acid, and to their use by way of couplers for the oxidation dyeing of keratinous fibres, especially human hair.

These compounds, when they are combined with para-phenylenediamines, surprisingly give beige to light brown hues or purple hues of greater or lesser redness, depending on the substitution of the 5-amino group of the chlorobenzene.

23 Claims, No Drawings

NEW CHLORO-META-PHENYLENEDIAMINES, THEIR USE AS COUPLERS IN THE OXIDATION DYEING OF KERATINOUS FIBRES, DYEING COMPOSITIONS FOR HAIR CONTAINING THESE COMPOUNDS AND DYEING PROCESS USING THE SAID

New chloro-meta-phenylenediamines, their use as couplers in the oxidation dyeing of keratinous fibres, dyeing compositions for hair containing these compounds and dyeing process using the said compositions.

The present invention relates to new chloro-meta-phenylenediamines, to their use as couplers in the oxidation dyeing of keratinous fibres, to the dyeing compositions for human hair containing these compounds by way of couplers, in combination with oxidation dye precursors, and to a dyeing process using the said compositions.

In the field of keratinous fibres, such as hair or furs, meta-phenylenediamines play an important part which has been known for a long time. They form part of the class of compounds commonly known as couplers.

These couplers are used in order to vary the hues obtained with oxidation dye precursors, in particular of the para type, such as para-phenylenediamines and para-aminophenols.

In general, the combination of meta-phenylenediamines with para-phenylenediamines in an oxidizing alkaline medium, and more especially in the presence of hydrogen peroxide, gives rise to compounds capable of imparting very strong blue colourations to keratinous fibres.

The combination of meta-phenylenediamines with para-aminophenols in an oxidizing alkaline medium, and more especially in the presence of hydrogen peroxide, normally gives rise to compounds capable of imparting red colourations to keratinous fibres.

In point of fact, the Applicant has found that, contrary to all expectations, certain meta-phenylenediamines, when they are combined with para-phenylenediamines in an alkaline medium, and more especially in the presence of hydrogen peroxide, enable unexpected hues, which can be beige to light brown hues or purple hues of greater or lesser redness, to be obtained on keratinous fibres. By coupling with para-aminophenols, these meta-phenylenediamines lead to light brown and yellow colours which are not without interest for those versed in the art, in cases where it is desired to obtain light hues or to soften excessively bright reds.

The subject of the present invention is hence the new compounds corresponding to the formula (I) below, or their addition salts with an acid:

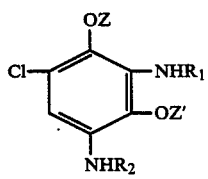

in which formula:

Z and Z' denote, independently of one another, an alkyl radical having from 1 to 4 carbon atoms or a hydroxyalkyl radical having from 2 to 4 carbon atoms, and $R_1$ and $R_2$ denote, independently of one another, a hydrogen atom, an alkyl radical having from 1 to 4 carbon atoms or a mono- or polyhydroxyalkyl radical having from 2 to 3 carbon atoms, with the proviso that, when $R_1$ and $R_2$ simultaneously denote a hydrogen atom, Z and Z' do not simultaneously denote a methyl radical.

Another subject of the invention is the use, by way of couplers, of the compounds of the formula (I'):

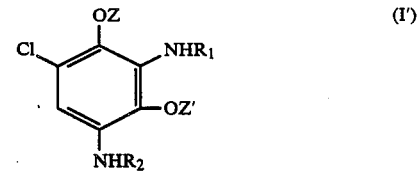

in which:

Z and Z' denote, independently of one another, an alkyl radical having from 1 to 4 carbon atoms or a hydroxyalkyl radical having from 2 to 4 carbon atoms, and $R_1$ and $R_2$ denote, independently of one another, a hydrogen atom, an alkyl radical having from 1 to 4 carbon atoms or a mono- or polyhydroxyalkyl radical having from 2 to 3 carbon atoms, or of their addition salts with an acid, in combination with oxidation dye precursors, for the dyeing of keratinous fibres and especially human hair.

The subject of the present invention is also a dyeing composition for keratinous fibres, and especially for human hair, comprising, in a cosmetically acceptable aqueous vehicle, at least one compound of the formula (I') above, or alternatively one of its salts with acids, by way of a coupler, in combination with at least one oxidation dye precursor of the para type.

The invention also relates to a hair dyeing process using such a dyeing composition.

Depending on the meaning of the radicals $R_1$ and $R_2$, the compounds of the formula (I) or (I') may be prepared according to the processes described below.

(1) Process for preparing the compounds (I) or (I') in which $R_1 = R_2 = H$

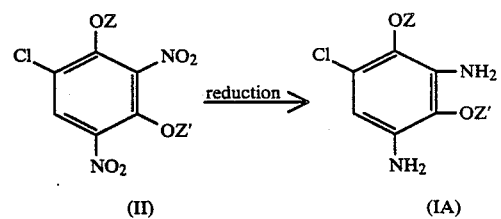

Z and Z' have the meanings stated above for the formula (I').

The compounds of the formula (II) are reduced with iron in acetic acid medium at a temperature of between 50° C. and 100° C.

(2) Process for preparing the compounds (I) or (I') in which $R_1 = R_2 \neq H$ and have the meanings stated in the formula (I).

The compounds ($I_A$) above are subjected to an alkylation or hydroxyalkylation reaction according to traditional processes for alkylation or hydroxyalkylation of aromatic amines.

(3) Process for preparing the compounds (I) or (I') in which $R_1 = H$ and $R_2 \neq H$ (compounds IB)

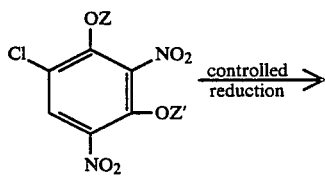

(II)

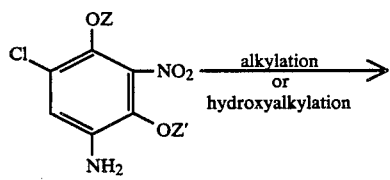

(III)

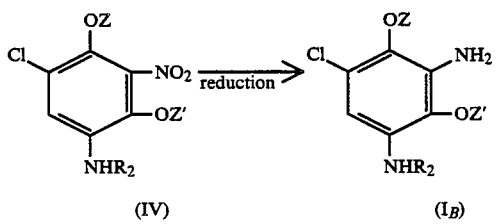

(IV)    (I$_B$)

Z, Z' and R$_2$ have the meanings stated in the formula (I).

The compound of formula (II) is subjected to a controlled reduction. Among known controlled reductions, there may be mentioned a reduction by transfer of hydrogen, in the presence of a catalyst such as palladium on charcoal and of cyclohexene as a hydrogen donor.

The compound of formula (III) thereby obtained is subjected to an alkylation or hydroxyalkylation reaction, and leads to the compound (IV).

The compound (IV) is reduced with iron in the presence of acetic acid at a temperature of between 50° C. and 100° C.

(4) Process for preparing the compounds (I) or (I') in which R$_1$=H and R$_2 \neq$H (compounds IC)

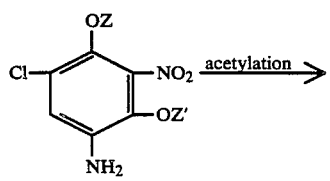

(III)

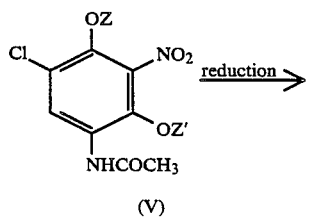

(V)

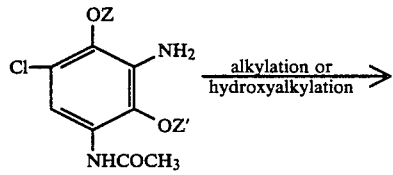

(VI)

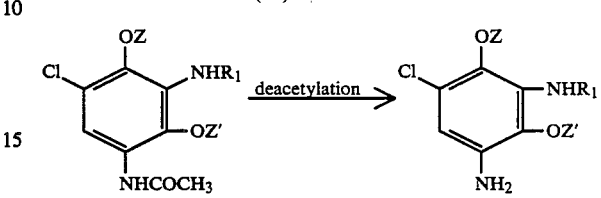

(VII)    (IC)

Z, Z' and R$_1$ have the meanings stated in the formula (I).

The compound of formula (III), prepared in the same manner as according to the preparation process (3), is acetylated with acetic anhydride at a temperature of between 20° and 100° C. The compound (V) is obtained.

The compound (V) is reduced to the compound (VI) in acetic acid medium with iron, at a temperature of between 50° and 100° C.

The compound (VI) is then alkylated or hydroxyalkylated according to processes known to lead to the compound (VII).

The latter is deacylated, and the compound of the formula (I) or (I') in which R$_1$ is other than H and R$_2$=H is thereby obtained.

(5) Process for preparing the compounds (I) or (I') in which R$_1 \neq$R$_2 \neq$H The compounds (I) or (I') in which R$_1$ and R$_2$ are other than H but have different meanings may be prepared by alkylation or hydroxyalkylation of the compounds (IB) or (IC) above, according to traditional methods.

The alkylation and hydroxyalkylation stages mentioned in the above preparation processes are known.

By way of alkylating agents, alkyl halides or dialkyl sulphates are used.

For the hydroxyalkylation, the preferred method consists in reacting β-chloroethyl chloroformate with the compound bearing the free amino group, and in converting the intermediate carbamate to an oxazolidone, which is then hydrolysed.

This process is described in French Patent Application 2,571,364.

The intermediate β-chloroethyl carbamate can also be subjected directly to the action of a strong inorganic base, such as sodium hydroxide or potassium hydroxide to give the compound (I) in which R$_1$ or R$_2$ is a β-hydroxyethyl radical.

The starting compounds of formula (II) may be obtained by one of the following processes.

Process 1

This process is described in "Recueil T. Chimiques Pays-Bas", R40, p. 451–471.

It consists in nitrating 1,2,4-trichlorobenzene with fuming nitric acid, optionally in the presence of sulphuric acid. 1,2,4-Trichloro-3,5-dinitrobenzene is obtained, of which the chlorine atoms at the 2- and 4-positions are then substituted by groups OZ and OZ' by reaction with the corresponding alkali metal alcoholate.

This process may be shown schematically in the following manner:

[Reaction scheme: 1,2-dichlorobenzene → Nitration → dichlorodinitrobenzene → ZOA then Z'OA → compound (II)]

A being an alkali metal.

Process 2

This consists in nitrating the 2,4-dialkoxychlorobenzene or 2,4-bis(hydroxyalkoxy)chlorobenzene with fuming nitric acid, optionally in the presence of sulphuric acid. The 2,4-dialkoxy-3,5-dinitrochlorobenzene or 2,4-bis(hydroxyalkoxy)-3,5-dinitrochlorobenzene, respectively, is obtained in a single stage.

This process may be shown schematically in the following manner:

[Reaction scheme: 2,4-dialkoxychlorobenzene → Nitration → compound (II)]

Process 3

This consists in alkylating or hydroxyalkylating 3,6-dichlorophenol or 3,4-dichlorophenol, in nitrating the compound obtained and finally in substituting a chlorine atom by an alkoxy or hydroxyalkoxy group by the action of the corresponding alkali metal alcoholate.

This process is advantageous, in particular, in the case where Z and Z' are not identical.

It may be summarized by the two schemes below:

(α)

[Reaction scheme: 2,5-dichlorophenol → alkylation → intermediate → nitration →]

[continued reaction scheme → Z'OA → compound (II)]

(β)

[Reaction scheme: 3,4-dichlorophenol → alkylation → intermediate → nitration → intermediate → ZOA → compound (II)]

A being an alkali metal.

By way of preferred compounds of the formula (I), there may be mentioned:

5-(β-hydroxyethyl)amino-3-amino-2,4-dimethoxychloro-benzene 5-amino-3-(β-hydroxyethyl)amino-2,4-dimethoxychlorobenzene 3,5-bis(β-hydroxyethyl)amino-2,4-dimethoxychlorobenzene 5-methylamino-3-amino-2,4-dimethoxychlorobenzene 3,5-diamino-2,4-diethoxychlorobenzene 3,5-diamino-2,4-bis(γ-hydroxypropoxy)chlorobenzene as well as their addition salts with an acid, and especially an inorganic acid such as hydrochloric acid, hydrobromic acid or sulphuric acid.

The dyeing compositions for keratinous fibres and especially for human hair, according to the present invention contain at least one compound of the formula (I'), or one of its addition salts with an acid, by way of a coupler, and at least one oxidation dye precursor of the para type, in a cosmetically acceptable aqueous vehicle.

By way of especially preferred couplers of the formula (I'), there may be mentioned:

5-(β-hydroxyethyl)amino-3-amino-2,4-dimethoxychlorobenzene 5-amino-3-(β-hydroxyethyl)amino-2,4-dimethoxychlorobenzene 3,5-bis(β-hydroxyethyl)amino-2,4-dimethoxychlorobenzene 5-methylamino-3-amino-2,4-dimethoxychlorobenzene 3,5-diamino-2,4-dimethoxychlorobenzene 3,5-diamino-2,4-diethoxychlorobenzene 3,5-diamino-2,4-bis(γ-hydroxypropoxy)chlorobenzene
as well as their addition salts with an acid, and especially an inorganic acid such as hydrochloric, hydrobromic or sulphuric acid.

The Applicant found, surprisingly, that the coupling of para-phenylenediamines with the couplers of formula (I') in which $R_2$ is other than a hydrogen atom, in an oxidizing medium, led to purple colours of greater or lesser redness on hair. The coupling of para-phenylenediamines with the couplers of the formula (I') in which $R_2$ denotes a hydrogen atom leads to beige hues which are useful for a formulary of light colours or for "softening" certain reds.

The compounds of the formula (I') or their salts, used with para-phenylenediamines, lead to hues which are stable to light, to inclement weather and to washing, after development in the presence of an oxidizing agent.

The oxidation dye precursor is chosen from benzene derivatives or heterocyclic derivatives such as, for example, pyridine, to which derivatives two amino groups or one amino group and one hydroxy group are bound in the para position. These dye precursors may be present in the dyeing compositions in the form of free bases or in the form of addition salts with acids.

Especially preferred oxidation dye precursors which are usable according to the invention are chosen from the para-phenylenediamines corresponding to the following general formula:

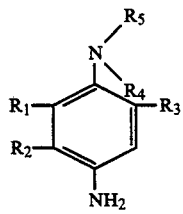

(VIII)

or the corresponding salts, in which formula $R_1$, $R_2$ and $R_3$ are identical or different and denote a hydrogen or halogen atom, an alkyl radical having 1 to 4 carbon atoms or an alkoxy radical having 1 to 4 carbon atoms, and $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ having from 1 to 4 carbon atoms, or alternatively $R_4$ and $R_5$ can form, together with the nitrogen atom to which they are linked, a piperidino or morpholino heterocycle, with the proviso that $R_1$ or $R_3$ denotes a hydrogen atom when $R_4$ and $R_5$ do not denote a hydrogen atom.

Among the compounds of formula (VIII) shown above, there may be mentioned p-phenylenediamine, p-tolylenediamine, methoxy-para-phenylenediamine, chloro-para-phenylenediamine, 2,6-dimethyl-para-phenylenediamine, 2,5-dimethyl-para-phenylenediamine, isopropyl-p-phenylenediamine, 2,3-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-bis(β-hydroxyethyl)-para-phenylenediamine, 3-methyl-4-amino-N,N-bis(β-hydroxyethyl)aniline, 3-chloro-4-amino-N,N-bis(β-hydroxyethyl)aniline, 4-amino-N-ethyl-N-(carbamylmethyl)aniline, 3-methyl-4-amino-N-ethyl-N-(carbamylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine and N-(4-aminophenyl)piperidine. These oxidation dye precursors of the para type may be introduced into the dyeing composition in the form of the free base or in the form of salts, such as in the form of a hydrochloride, hydrobromide or sulphate.

The compound of the formula (I') or its salts may also be used with para-aminophenols to give light brown to yellow hues which are stable to light, to inclement weather and to washing, after development in the presence of an oxidizing agent. Among para-aminophenols, there may be mentioned para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol and 3-methoxy-4-aminophenol.

The compound of the formula (I') or its salts may also be used with heterocyclic para oxidation dye precursors, among which 2,5-diaminopyridine, 2-hydroxy-5-aminopyridine and tetraaminopyrimidine may be mentioned.

The dyeing compositions according to the invention can also contain oxidation dye precursors of the ortho type, such as ortho-aminophenols, ortho-phenylenediamines and ortho-diphenols. There may be mentioned, for example, 1-amino-2-hydroxybenzene, 6-methyl-1-hydroxy-2-aminobenzene and 4-methyl-1-amino-2-hydroxybenzene.

The dyeing compositions according to the invention containing the compound (I') or its salts can optionally contain other couplers which are known per se, such as meta-diphenols, meta-aminophenols, meta-phenylenediamines, meta-acylaminophenols, meta-ureidophenols, meta-carbalkoxyaminophenols, α-naphthol, and couplers possessing an active methylene group such as β-keto compounds and pyrazolones.

There may be mentioned, in particular, by way of example, 2,4-dihydroxyphenoxyethanol, 2,4-dihydroxyanisole, meta-aminophenol, resorcinol monomethyl ether, 2-methyl-5-aminophenol, 2-methyl-5-[N-(β-hydroxyethyl)-amino]phenol, 2-methyl-5-[N-(β-mesylaminoethyl)amino]phenol, 2,6-dimethyl-3-aminophenol, 6-hydroxybenzomorpholine, 2,4-diaminophenoxyethanol, 6-aminobenzomorpholine, 2-[N-(β-hydroxyethyl)amino]-4-aminophenoxyethanol, 2-amino-4-[N-(β-hydroxyethyl)amino]anisole, 2,4-diaminophenyl-β,γ-dihydroxypropyl ether, 2,4-diaminophenoxyethylamine, 3,4-methylenedioxyphenol and 3,4-methylenedioxyaniline, and their salts.

As is well known, it is possible to add to these compositions, for the purpose of altering the hue or enriching with glints the colourations provided by the oxidation dye precursors, direct dyes such as azo or anthraquinone dyes or nitro derivatives of the benzene series.

The para compounds and the couplers used in the dyeing compositions according to the invention preferably represent collectively from 0.1 to 7% by weight of the said composition. The concentration of the compound (I') can vary between 0.05 and 3.5% of the total weight of the composition.

The cosmetically acceptable aqueous vehicle has a pH which can vary between 8 and 11, and it is preferably between 9 and 11.

It is adjusted to the desired value by means of an alkalinizing agent such as ammonia solution, alkali metal carbonates or alkanolamines such as mono-, di- or triethanolamine.

The dyeing compositions according to the invention, in their preferred embodiment, also contain anionic, cationic, nonionic or amphoteric surfactants, or mixtures thereof. Among these surfactants, there may be mentioned, more especially, alkylbenzenesulphonates, alkylnaphthalenesulphonates, fatty alcohol sulphates, ether sulphates and sulphonates, quaternary ammonium salts such as trimethylcetylammonium bromide and cetylpyridinium bromide, fatty acid ethanolamides, optionally oxyethylenated, polyoxyethylenated acids, alcohols and amines, polyglycerolated alcohols, polyoxyethylenated or polyglycerolated alkylphenols and also polyoxyethylenated alkyl sulphates. The surfactants are present in the compositions according to the invention in proportions of between 0.5 to 40% by weight, and preferably between 4 and 30% by weight, relative to the total weight of the composition.

These compositions can also contain organic solvents for solubilizing any compounds which are insufficiently soluble in water. Among these solvents, there may be mentioned, by way of example, $C_1$-$C_4$ lower alkanols such as ethanol and isopropanol; glycerol; glycols or glycol ethers such as 2-butoxyethanol, ethylene glycol, propylene glycol, diethylene glycol monoethyl ether and monomethyl ether; and also similar products, and mixtures thereof. The solvents are preferably present in a proportion of between 1 and 40% by weight, and especially between 5 and 30% by weight, relative to the total weight of the composition.

The thickening agents which can be added to the compositions according to the invention are selected, in particular, from the group composed of sodium alginate, gum arabic, cellulose derivatives such as methylcellulose, hydroxyethylcellulose, hydroxypropylcellulose, hydroxymethylcellulose and carboxymethylcellulose, acrylic acid polymers and xanthan gum. It is also possible to use inorganic thickening agents such as bentonite. These thickening agents are preferably present in proportions of between 0.1 to 5% by weight, and especially between 0.5 and 5% by weight, relative to the total weight of the composition.

The compositions can contain antioxidant agents chosen, in particular, from sodium sulphite, thioglycolic acid, sodium bisulphite, ascorbic acid and hydroquinone. These antioxidant agents are present in the composition in proportions of between 0.05 and 1.5% by weight, relative to the total weight of the composition.

Other adjuvants which are usable according to the invention are, for example, penetrating agents, sequestering agents, buffers and perfumes.

The dyeing compositions according to the invention may be presented in various forms, such as in the form of liquids, creams or gels, or in any other form suitable for carrying out a dyeing of keratinous fibres, and in particular human hair. They can also be packaged in aerosol cans in the presence of a propellent agent.

The dyeing compositions according to the invention, containing an oxidation dye precursor of the para type and the compound (I') or one of its salts, are used in a hair dyeing process employing development with an oxidizing agent.

According to this process, the dyeing composition described above is mixed at the time of use with a sufficient quantity of an oxidizing solution, and the mixture obtained is then applied on the hair.

The oxidizing solution contains oxidizing agents such as hydrogen peroxide, urea peroxide or persalts such as ammonium persulphate. A "20 volumes" hydrogen peroxide solution is preferably used.

The mixture obtained is applied on the hair and left in place for 10 to 40 minutes, and preferably 15 to 30 minutes, after which the hair is rinsed, washed with shampoo, rinsed again and dried.

Another process employing the compound (I') according to the invention consists in dyeing the hair in accordance with a multi-stage process, according to which, in a first stage, the para oxidation dye precursor is applied by means of a composition defined above, and, in a second stage, compound (I') is applied. The oxidizing agent is present in the composition applied in the second stage, or is alternatively applied on the hair itself in a third stage, the conditions of exposure, drying and washing being identical to those described in the above process.

The examples below serve to give a better illustration of the invention, but under no circumstances limit the scope of the latter.

Example of preparation 1

Preparation of
5-($\beta$-hydroxyethyl)amino-3-amino-2,4-dimethoxychlorobenzene dihydrochloride

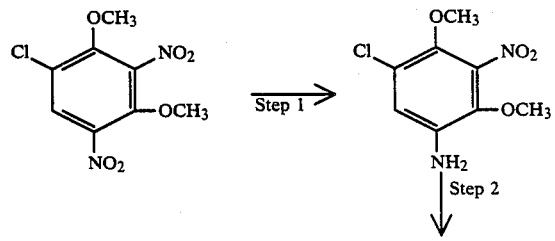

-continued

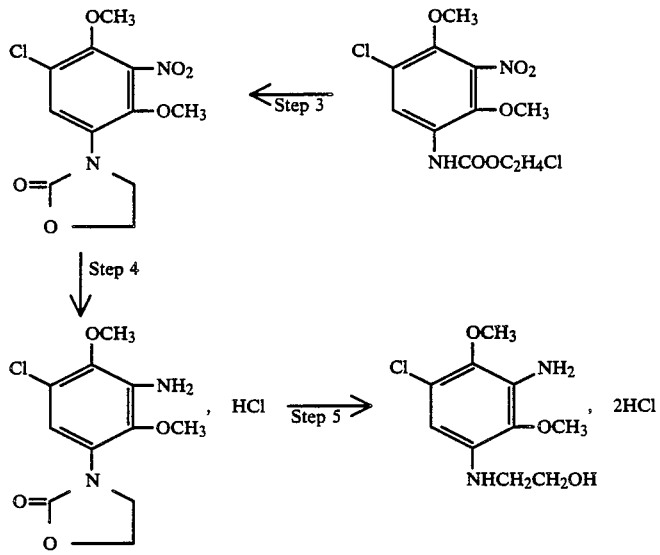

Step 1

Preparation of 5-amino-2,4-dimethoxy-3-nitrochlorobenzene

The mixture consisting of 0.2 mole (52.5 g) of 3,5-dinitro-2,4-dimethoxychlorobenzene, 15.9 g of palladium on charcoal (10%) in 260 ml of absolute ethanol containing 110 ml of cyclohexene was heated to reflux for 1 hour. The catalyst was removed by filtration. After evaporation to dryness under vacuum, an oil was obtained which crystallized after an addition of iced water. After thorough draining and drying, the product obtained was recrystallized from a benzene and cyclohexane mixture. It melted at 68° C.

Analysis of the product obtained gave the following results:

| Analysis | Calculated for $C_8H_9N_2O_4Cl$ | Found |
|---|---|---|
| % C | 41.28 | 41.10 |
| % H | 3.87 | 3.90 |
| % N | 12.04 | 11.98 |
| % O | 27.52 | 27.68 |
| % Cl | 15.27 | 14.99 |

Step 2

Preparation of 5-(β-chloroethoxycarbonyl)amino-2,4-dimethoxy-3-nitrochlorobenzene 0.05 mole (11.7 g) of 5-amino-2,4-dimethoxy-3-nitrochlorobenzene was dissolved in 50 ml of dioxane. 5 g of calcium carbonate were added and then the temperature was raised to the region of 90° C. 0.05 mole (7.2 g) of β-chloroethyl chloroformate was then introduced with stirring. Upon completion of the addition, stirring was maintained for 30 additional minutes at 90° C. The inorganic salts present in the reaction mixture were removed by filtration while hot. After addition of iced water to the filtrate, the expected product crystallized. The product obtained was thoroughly drained and washed with water. After drying, it was recrystallized from ethanol. It melted at 93° C.

Analysis of the product obtained gave the following results:

| | Calculated for $C_{11}H_{12}Cl_2N_2O_6$ | Found |
|---|---|---|
| % C | 38.94 | 38.78 |
| % H | 3.54 | 3.53 |
| % N | 8.26 | 8.35 |
| % O | 28.32 | 28.40 |
| % Cl | 20.94 | 21.03 |

Step 3

Preparation of N-[(3'-chloro-4',6'-dimethoxy-5'-nitro)phenyl]-1,3-oxazolidine-2-one 0.03 mole (10.2 g) of β-chloroethyl carbamate obtained according to the operating procedure described in step 2 was heated to 70° C. in 50 ml of methanol. 0.03 mole of sodium methylate as a 30% solution in methanol was added rapidly. Heating was maintained for 15 additional minutes upon completion of the addition. The inorganic salts were removed by filtration. From the filtrate which was cooled and diluted with iced water, the expected product which had crystallized was isolated by filtration. After drying, it was recrystallized from ethanol. It melted at 133° C.

Analysis of the product obtained gave the following results:

| | Calculated for $C_{11}H_{11}ClN_2O_6$ | Found |
|---|---|---|
| % C | 43.64 | 43.81 |
| % H | 3.64 | 3.64 |
| % N | 9.26 | 9.37 |
| % O | 31.74 | 31.62 |
| % Cl | 11.74 | 11.74 |

Step 4

Preparation of N-[(3'-chloro-4',6'-dimethoxy-5'-amino)-phenyl]-1,3-oxazolidine-2-one hydrochloride 12 g of powdered iron which had been reduced with hydrogen were added to 60 ml of water containing 3 ml of acetic acid and which has been previously heated in a boiling water bath, and 0.02 mole (6.05 g) of 1,3-oxazolidine-2-one obtained according to the operating procedure described in the previous step was added gradually, with stirring. Upon completion of the additions, heating was maintained for 15 additional minutes. The iron slurries were removed from the reaction mixture by filtration while hot. The reaction mixture freed from the iron slurries, was extracted with ethyl acetate. The ethyl acetate phase was washed with water and dried over sodium sulphate. The expected product was precipitated by addition of a 7N hydrochloric acid solution in absolute ethanol.

Analysis of the product obtained gave the following results:

|  | Calculated for $C_{11}H_{14}N_2O_4Cl_2$ | Found |
|---|---|---|
| % C | 42.72 | 42.59 |
| % H | 4.53 | 4.64 |
| % N | 9.06 | 8.96 |
| % O | 20.71 | 20.60 |
| % Cl | 22.98 | 22.87 |

Step 5

Preparation of 5-($\beta$-hydroxethyl)amino-3-amino-2,4-dimethoxychlorobenzene dihydrochloride 0.03 mole (0.3 g) of N-[(3'-chloro-4',6'-dimethoxy-5'-amino)-phenyl]-1,3-oxazolidine-2-one hydrochloride obtained according to the operating procedure described in the previous step was added to 10 ml of water containing 10 ml of ethanol. 18 ml of 10N sodium hydroxide were added to this solution. The mixture was heated for 30 minutes at 80° C. After cooling and phase separation, the upper phase was diluted with ethyl acetate. After washing with water and drying over sodium sulphate, 14 ml of a 7N hydrochloric acid solution in absolute ethanol were added. The expected product precipitated. It was recrystallized from an aqueous alcoholic solution of hydrochloric acid.

Analysis of the product obtained gave the following results:

|  | Calculated for $C_{10}H_{17}N_2O_3Cl_3$ | Found |
|---|---|---|
|  | 37.56 | 37.44 |
| % H | 5.32 | 5.24 |
| % N | 8.76 | 8.83 |
| % O | 15.02 | 15.21 |
| % Cl | 33.33 | 33.07 |

Example of preparation 2

Preparation of 5-amino-3-($\beta$-hydroxyethyl)amino-2,4-dimethoxychlorobenzene dihydrochloride

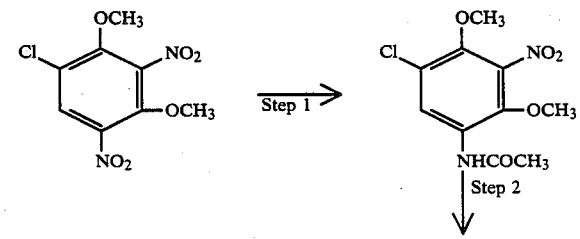

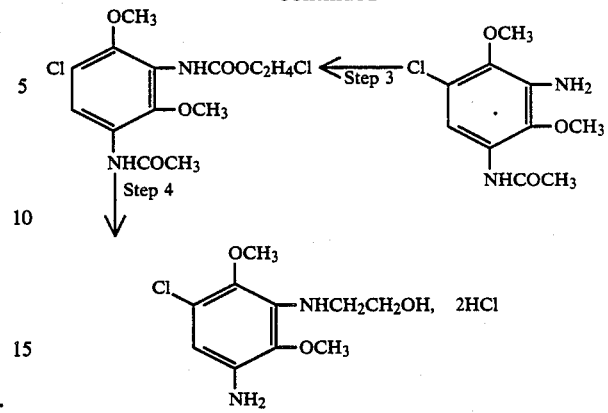

Step 1

Preparation of 5-acetamido-2,4-dimethoxy-3-nitrochlorobenzene 330 ml of acetic anhydride containing a few drops of sulphuric acid were heated to 70° C. 0.7 mole (163 g) of 5-amino-2,4-dimethoxy-3-nitrochlorobenzene prepared according to the operating procedure described in Example of preparation 1 (step 1) was added with stirring.

Upon dilution of the reaction mixture with iced water, the expected product precipitated. Recrystallized from 96° strength ethanol, it melted at 115° C.

Analysis of the product obtained gave the following results:

|  | Calcultated for $C_{10}H_{11}N_2O_5Cl$ | Found |
|---|---|---|
| % C | 43.72 | 43.67 |
| % H | 4.01 | 4.07 |
| % N | 10.20 | 10.17 |
| % O | 29.14 | 29.04 |
| % Cl | 12.93 | 12.98 |

Step 2

Preparation of 5-acetamido-2,4-dimethoxy-3-aminochlorobenzene 253 g of powdered iron which had been reduced with hydrogen were added to 760 ml of water containing 13 ml of acetic acid and which had been previously heated to 80° C., and then 0.46 mole (126.5 g) of 5-acetamido-2,4-dimethoxy-3-nitrochlorobenzene prepared in the previous step was added gradually, with stirring. Upon completion of the additions, the reaction mixture was maintained in a boiling water bath for 15 minutes. After cooling, the reaction mixture was centrifuged. The iron slurries after being separated from the liquid phase were extracted with ethyl acetate. The ethyl acetate phase which was washed with water and then dried over sodium sulphate was diluted with 100 ml of a 7N hydrochloric acid solution in absolute ethanol. The expected product, which precipitated in the form of hydrochloride, was thoroughly drained. It was dissolved in the minimum amount of water. After neutralization, the expected product precipitated. Recrystallized from alcohol, it melted at 113° C.

Analysis of the product obtained gave the following results:

|  | Calculated for $C_{10}H_{13}ClN_2O_3$ | Found |
|---|---|---|
| % C | 49.08 | 49.12 |
| % H | 5.32 | 5.31 |
| % N | 11.45 | 11.50 |
| % O | 19.63 | 19.74 |
| % Cl | 14.52 | 14.49 |

Step 3

Preparation of 5-acetamido-3-($\beta$-chloroethoxycarbonyl)-amino-2,4-dimethoxychlorobenzene 0.05 mole (14 g) of 5-acetamido-3-amino-2,4-dimethoxychlorobenzene hydrochloride obtained according to the previous step, followed by 5.5 ml of 10N sodium hydroxide were added to 70 ml of dioxane. The temperature was raised to the region of 90° C. and then 5 g of calcium carbonate were added. 7.55 g of $\beta$-chloroethyl chloroformate were then introduced with stirring. Upon completion of the addition, heating was maintained for 30 minutes at 90° C. The reaction mixture was diluted with an ice/water mixture after cooling. The expected product precipitated after acidification of the reaction mixture. Recrystallized from ethanol, it melted at 148° C.

Analysis of the product obtained gave the following results:

|  | Calculated for $C_{13}H_{16}Cl_2N_2O_5$ | Found |
|---|---|---|
| % C | 44.44 | 44.46 |
| % H | 4.56 | 4.54 |
| % N | 7.98 | 7.95 |
| % O | 22.79 | 22.66 |
| % Cl | 20.23 | 20.29 |

Step 4

Preparation of 5-amino-3-($\beta$-hydroxyethyl)amino-2,4-dimethoxychlorobenzene dihydrochloride The mixture consisting of 0.25 mole (88 g) of $\beta$-chloroethyl carbamate obtained in the previous step and of 250 ml of 10N sodium hydroxide in 10 ml of water containing 15 ml of ethanol was heated to reflux. After heating for 1 hour the reaction mixture which was cooled and neutralized was extracted with ethyl acetate. The ethyl acetate phases taken together were evaporated under vacuum after having been washed and dried over sodium sulphate. The solids content obtained was dissolved in isopropyl ether. The expected product precipitated upon addition of a 7N hydrochloric acid solution in absolute ethanol. It was recrystallized from an aqueous-alcoholic mixture containing hydrochloric acid.

Analysis of the product obtained gave the following results:

|  | Calculated for $C_{10}H_{17}N_2O_3Cl_3$ | Found |
|---|---|---|
| % C | 37.56 | 37.59 |
| % H | 5.32 | 5.36 |
| % N | 8.76 | 8.68 |
| % O | 15.02 | 15.24 |
| % Cl | 33.33 | 33.21 |

Example of preparation 3

Preparation of the 3,5-diamino-2,4-dimethoxychlorobenzene dihydrochloride

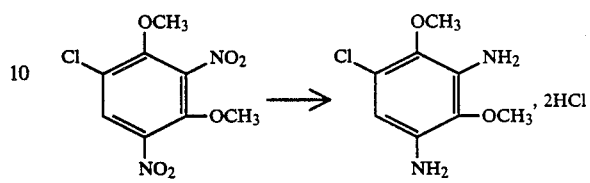

100 g of powdered iron which has been reduced with hydrogen were added to 270 ml of water containing 27 ml of acetic acid and which had been previously heated to 80° C., and then 0.25 mole (66 g) of 3,5-dinitro-2,4-dimethoxychlorobenzene was added gradually, with stirring. Upon completion of the additions, the reaction mixture was maintained in a boiling water bath for 30 additional minutes. After cooling, the reaction mixture was centrifuged. The iron slurries which contained the expected product were taken up with acetone under vigorous mixing. Upon filtration of the iron slurries followed by washing with acetone, the expected product precipitated from the acetone filtrate upon addition of hydrochloric acid solution in ethanol. After thorough draining and washing, the expected product was recrystallized while hot from a hydrochloric acid and water mixture.

Analysis of the product obtained gave the following results:

|  | Calculated for $C_8H_{13}N_2Cl_3O_2$ | Found |
|---|---|---|
| % C | 34.85 | 34.85 |
| % H | 4.72 | 4.82 |
| % N | 10.16 | 10.03 |
| % O | 11.62 | 11.80 |
| % Cl | 38.66 | 38.46 |

Example of preparation 4

Preparation of the 3,5-bis($\beta$-hydroxyethyl)amino-2,4-dimethoxychlorobenzene dihydrochloride

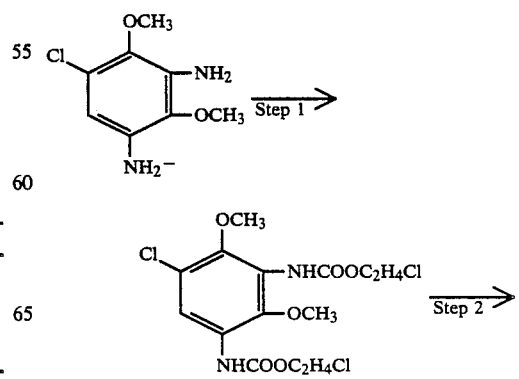

-continued

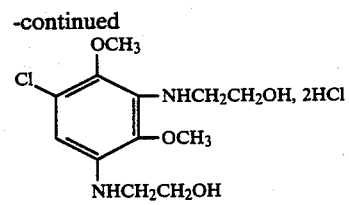

Step 1

Preparation of the 3,5-di-(β-chloroethoxycarbonyl)amino-2,4-dimethoxy-chlorobenzene 0.15 mole (41.3 g) of 3,5-diamino-2,4-dimethoxy-chlorobenzene dihydrochloride obtained in Example 3, followed by 30 ml of 10N sodium hydroxide was added to 200 ml of dioxane. The temperature was raised to the region of 80° C., and then 15 g of calcium carbonate were added. 43 g of β-chloroethyl chloroformate were then introduced with stirring. Upon completion of the addition, heating was maintained at 90° C. for 15 minutes. The inorganic salts were removed from the reaction mixture by filtration. The expected product crystallized slowly upon dilution of the reaction mixture with iced water. Recrystallized from 96° strength ethanol, it melted at 87° C.

Analysis of the product obtained gave the following results:

|  | Calculated $C_{14}H_{17}N_2O_6Cl_3$ | Found |
|---|---|---|
| % C | 40.43 | 40.41 |
| % H | 4.09 | 4.08 |
| % N | 6.74 | 6.82 |
| % O | 23.10 | 23.06 |
| % Cl | 25.63 | 25.51 |

Step 2

Preparation of the 3,5-bis-(β-hydroxyethyl)amino-2,4-dimethoxychlorobenzene dihydrochloride 0.08 mole (33.3 g) of the compound prepared in the previous step followed by 72 ml of 10N sodium hydroxide diluted with 36 ml of water was added to 72 ml of ethanol. After 30 minutes of heating under reflux, the ethanol was removed from the reaction mixture by distillation under reduced pressure. The reaction mixture was neutralized and then extracted with ethyl acetate. The ethyl acetate phases were washed with water. 30 ml of a 7N hydrochloric acid solution in absolute ethanol were added. The expected product precipitated slowly in the form of a hemihydrate. It was recrystallized from ethanol.

Analysis of the product obtained gave the following results:

|  | Calculated for $C_{12}H_{21}N_2O_4Cl_3$ ½ $H_2O$ | Found |
|---|---|---|
| % C | 38.65 | 38.55 |
| % H | 6.17 | 5.84 |
| % N | 7.59 | 7.43 |
| % O | 19.32 | 19.28 |
| % Cl | 28.59 | 28.50 |

Example of preparation 5

Preparation of 5-methylamino-3-amino-2,4-dimethoxy-chlorobenzene dihydrochloride

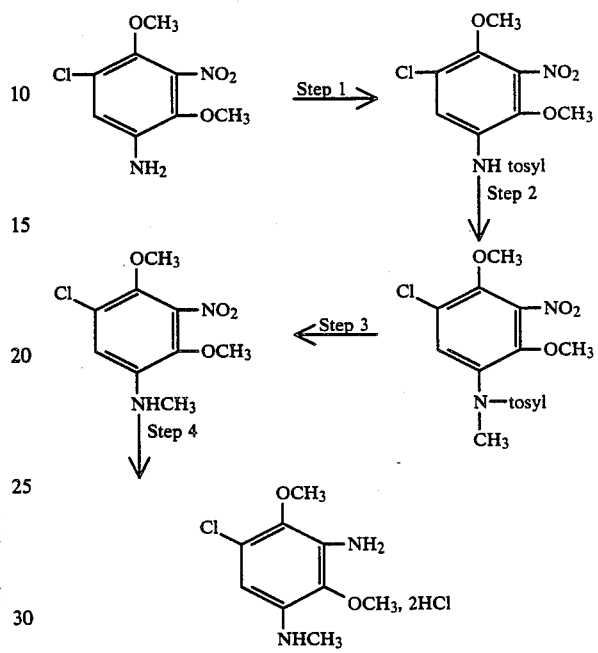

Step 1

Preparation of 5-(N-tosylamino)-2,4-dimethoxy-3-nitrochlorobenzene 0.11 mole (21 g) of p-toluenesulphochloride was added gradually at 40° C. to a solution of 0.1 mole (23.35 g) of 5-amino-2,4-dimethoxy-3-nitrochlorobenzene. Stirring was continued for 15 minutes at 40° C. upon completion of the addition. The reaction mixture was diluted with iced water. Upon acidification with concentrated hydrochloric acid, the expected product precipitated. After thorough draining, washing with water followed by alcohol, the product was dried. It was recrystallized from ethanol.

Analysis of the product obtained gave the following results:

| Analysis | Calculated for $C_{15}H_{15}N_2O_6SCl$ | Found |
|---|---|---|
| C % | 46.57 | 46.49 |
| H % | 3.88 | 3.90 |
| N % | 7.24 | 7.38 |
| O % | 24.84 | 24.56 |
| S % | 8.28 | 8.17 |
| Cl % | 9.18 | 9.35 |

Step 2

Preparation of 5-(N-tosyl-N-methylamino)-2,4-dimethoxy-3-nitro-chlorobenzene 0.022 mole (2.1 ml) of methyl sulphate was added at 30°-35° C. to a solution of 0.02 mole (7.7 g) of 5-(N-tosylamino)-2,4-dimethoxy-3-nitrochlorobenzene prepared in the previous step in 25 ml of a normal solution of sodium hydroxide. Stirring was continued for 15 minutes after completion of the addition. The expected product precipitated upon dilution of the reaction mixture with iced water. After thorough draining and washing with water, the product obtained was recrystallized from alcohol.

Analysis of the product obtained gave the following results:

| Analysis | Calculated for $C_{16}H_{17}N_2O_6SCl$ | Found |
| --- | --- | --- |
| C % | 47.94 | 47.96 |
| H % | 4.24 | 4.28 |
| N % | 6.99 | 7.00 |
| O % | 23.97 | 23.94 |
| S % | 7.99 | 7.84 |
| Cl % | 8.86 | 8.91 |

Step 3

Preparation of 5-methylamino-2,4-dimethoxy-3-nitrochlorobenzene 0.025 mole (10 g) of the compound prepared according to the previous step was added gradually to 20 ml of concentrated sulphuric acid, the temperature being maintained at 20° C. 15 minutes after completion of the addition, the reaction mixture was diluted with an ice-/water mixture. The expected product, which precipitated, was thoroughly drained, washed with water, dried under vacuum in the presence of $P_2O_5$. It was recrystallized from cyclohexane. It melted at 57° C.

Analysis of the product obtained gave the following results:

| Analysis | Calculated for $C_9H_{11}N_2O_4Cl$ | Found |
| --- | --- | --- |
| C % | 43.81 | 43.77 |
| H % | 4.46 | 4.55 |
| N % | 11.36 | 11.35 |
| O % | 25.96 | 26.12 |
| Cl | 14.40 | 14.36 |

Step 4

Preparation of 3-amino-5-methylamino-2,4-dimethoxychlorobenzene dihydrochloride 50 g of powdered iron which had been reduced with hydrogen were added to 200 ml of water containing 2.5 ml of acetic acid which had been previously heated in a boiling water bath, and 0.1 mole (24.65 g) of 5-methylamino-2,4-dimethoxy-3-nitrochlorobenzene obtained according to the operating procedure of step 3 was added gradually, with stirring. Upon completion of the additions, heating was maintained for 15 additional minutes. The reaction mixture was centrifuged, the expected product was extracted from the iron slurries with ethyl acetate. The ethyl acetate phases were washed with water, and then dried over anhydrous sodium sulphate. Upon addition of 43 ml of a 7N hydrochloric acid solution in ethanol, the expected product was precipitated. After thorough draining of the precipitate, washing with ethanol and drying, the product was recrystallized from an aqueous-alcoholic solution of hydrochloric acid.

Analysis of the product obtained gave the following results:

| Analysis | Calculated for $C_9H_{15}N_2O_2Cl_3$ | Found |
| --- | --- | --- |
| C % | 37.31 | 37.21 |
| H % | 5.18 | 5.23 |
| N % | 9.67 | 9.54 |
| O % | 11.05 | 11.10 |
| Cl % | 36.79 | 36.86 |

Example of preparation 6

Preparation of 3,5-diamino-2,4-diethoxychlorobenzene dihydrochloride

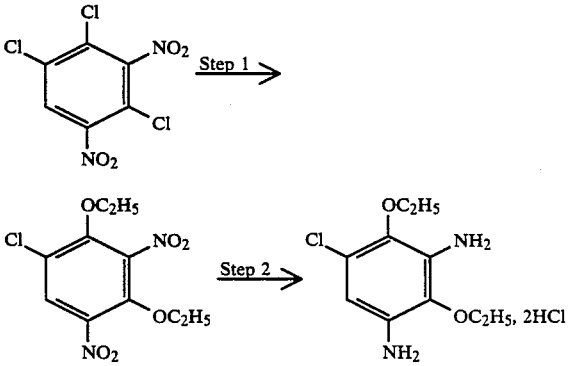

Step 1

Preparation of 3,5-dinitro-2,4-diethoxychlorobenzene 0.1 mole (27.15 g) of 3,5-dinitro-1,2,4-trichlorobenzene was heated to 75° C. in 110 ml of absolute ethanol. 0.2 mole of a 15% solution of sodium ethylate was added in absolute ethanol. Upon completion of the addition, the reaction mixture was heated for 30 minutes at 75° C. and then diluted with 300 g of an ice/water mixture. The expected product precipitated. After drying under vacuum and recrystallization from isopropyl ether, it melted at 78° C.

Analysis of the product obtained gave the following results:

| Analysis | Calculated for $C_{10}H_{11}N_2O_6Cl$ | Found |
| --- | --- | --- |
| C % | 41.31 | 41.22 |
| H % | 3.79 | 3.81 |
| N % | 9.64 | 9.65 |
| O % | 33.05 | 32.88 |
| Cl % | 12.22 | 12.07 |

Step 2

Preparation of 3,5-diamino-2,4-diethoxychlorobenzene dihydrochloride 170 g of powdered iron which had been reduced with hydrogen were added to 450 ml of water containing 8.5 ml of acetic acid which had previously been heated to 80° C., and then 0.3 mole (87 g) of 3,5-dinitro-2,4-diethoxychlorobenzene was added gradually, with stirring. Upon completion of the additions, the reaction mixture was maintained in a boiling water bath for 30 additional minutes. After cooling, the reaction mixture was centrifuged. The iron slurries were made to a paste again with ethyl acetate, and the mother liquors were extracted with ethyl acetate. The ethyl acetate phases joined together were washed with water and then dried over $Na_2SO_4$. Upon addition of a hydrochloric acid solution in ethanol, the expected product precipitated. After thorough draining, it was washed with acetone. It was recrystallized from an aqueous-alcoholic solution of hydrochloric acid.

Analysis of the product obtained gave the following results:

| Analysis | Calculated for $C_{10}H_{17}N_2O_2Cl_3$ | Found |
|---|---|---|
| C % | 39.54 | 39.67 |
| H % | 5.60 | 5.64 |
| N % | 9.23 | 9.26 |
| O % | 10.54 | 10.48 |
| Cl % | 35.09 | 35.26 |

Example of preparation 7

Preparation of 3,5-diamino-2,4-bis(γ-hydroxypropoxy)-chlorobenzene dihydrochloride

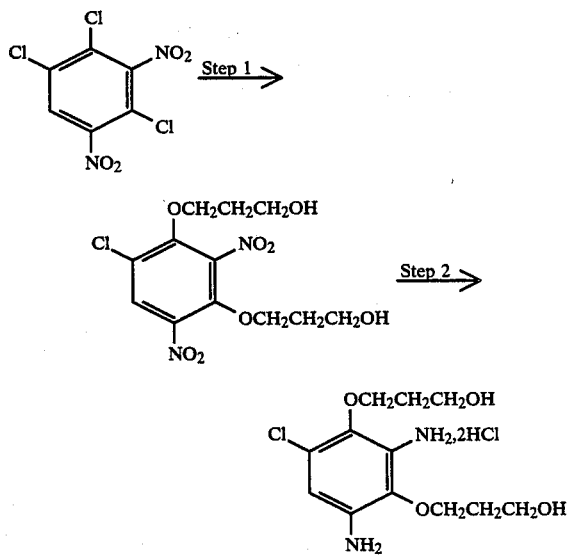

Step 1

Preparation of 3,5-dinitro-2,4-bis(γ-hydroxypropoxy)-chlorobenzene 1 mole (271.5 g) of 3,5-dinitro-1,2,4-trichlorobenzene was added to 700 ml of 1,3-propanediol at 85° C. 2 moles of powdered potassium hydroxide in 280 ml of 1,3-propanediol were added over 30 minutes. The reaction mixture was heated for 1 hour at 85° C. upon completion of the addition. After cooling, the expected product was filtered off, washed with water, and then dissolved in 1.5 liters of ethyl acetate which, after washing with water, was dried over sodium sulphate. After concentration to dryness, a precipitate was obtained which, after having been recrystallized from isopropyl ether, melted at 90° C.

Analysis of the product obtained gave the following results:

| Analysis | Calculated for $C_{12}H_{15}N_2O_8Cl$ | Found |
|---|---|---|
| C % | 41.08 | 41.12 |
| H % | 4.28 | 4.33 |
| N % | 7.99 | 8.04 |

-continued

| Analysis | Calculated for $C_{12}H_{15}N_2O_8Cl$ | Found |
|---|---|---|
| O % | 36.52 | 36.45 |
| Cl % | 10.13 | 10.09 |

Step 2

Preparation of 3,5-diamino-2,4-bis(γ-hydroxypropoxy)-chlorobenzene dihydrochloride 250 g of powdered iron which had been reduced with hydrogen were added to 700 ml of water containing 10 ml of acetic acid which had been previously heated to 95° C., and 0.34 mole (119 g) of 3,5-dinitro-2,4-bis(γ-hydroxypropoxy)chlorobenzene was added gradually with stirring. Upon completion of the additions, the reaction mixture was maintained for 10 additional minutes at 95° C. After cooling, 1 liter of ethyl acetate was added. The reaction mixture was filtered off in order to remove the iron slurries. The ethyl acetate phase, which was separated from the aqueous phase, was, after washing with water, and drying over sodium sulphate, evaporated off to dryness. The solids content obtained in this manner was taken up with a hydrochloric acid solution in absolute ethanol. The expected product precipitated. After thorough draining followed by drying, analysis of the product obtained gave the following results:

| Analysis | Calculated for $C_{12}H_{21}N_2O_4Cl_3$ | Found |
|---|---|---|
| C % | 39.62 | 39.49 |
| H % | 5.78 | 5.67 |
| N % | 7.70 | 7.56 |
| O % | 17.61 | 17.81 |
| Cl % | 29.30 | 29.26 |

Application Example 1

The following dyeing mixture is prepared:

| | |
|---|---|
| 3,5-Diamino-2,4-dimethoxychlorobenzene dihydrochloride | 0.68 g |
| p-Phenylenediamine | 0.27 g |
| Oleyl alcohol polyglycerolated with 2 moles of glycerol | 4.5 g |
| Oleyl alcohol polyglycerolated with 4 moles of glycerol | 4.5 g |
| ETHOMEEN 0 12 - company ARMOON HESS CHEMICAL Ltd (oleylamine oxyethynated with 12 moles of EO) | 4.5 g |
| COMPERLAN KD - company HENKEL (coconut diethanolamide) | 9 g |
| Propylene glycol | 4 g |
| 2-Butoxyethanol | 8 g |
| Ethanol, 96° strength | 6 g |
| MASQUOL DTPA - company PROTEX | 2 g |
| Hydroquinone | 0.15 g |
| Sodium bisulphite solution, 35° Be | 1.3 g |
| Ammonia solution, 22° Be | 10 g |
| Water qs | 100 g |
| pH: 10 | |

At the time of use, 100 g of "20 volumes" hydrogen peroxide are added. When applied for 20 minutes at 35° C. on bleached hair, the mixture imparts to the latter, after shampooing and rinsing, a slightly yellow dark grey-brown colouration.

Application Example 2

The following dyeing mixture is prepared:

| | |
|---|---|
| 3,5-Bis(β-hydroxyethyl)amino-2,4-dimethoxychlorobenzene dihydrochloride | 0.91 g |
| p-Phenylenediamine | 0.27 g |
| Oleyl alcohol polyglycerolated with 2 moles of glycerol | 4.5 g |
| Oleyl alcohol polyglycerolated with 4 moles of glycerol | 4.5 g |
| ETHOMEEN 0 12 - company ARMOON HESS CHEMICAL Ltd (oleylamine oxyethylenated with 12 moles of EO) | 4.5 g |
| COMPERLAN KD - company HENKEL (coconut diethanolamide) | 9 g |
| Propylene glycol | 4 g |
| 2-Butoxyethanol | 8 g |
| Ethanol, 96° strength | 6 g |
| MASQUOL DTPA - company PROTEX (pentasodium salt of diethylenetriaminepentaacetic acid | 2 g |
| Hydroquinone | 0.15 g |
| Sodium bisulphite solution, 35° Be | 1.3 g |
| Ammonia solution, 22° Be | 10 g |
| Water qs | 100 g |
| pH: 10 | |

At the time of use, 100 g of "20 volumes" hydrogen peroxide are added. When applied for 20 minutes at 35° C. on bleached hair, the mixture imparts to the latter, after shampooing and rinsing, a dark red-purple colouration.

Application Example 3

The following dyeing mixture is prepared:

| | |
|---|---|
| 3-Amino-5-methylamino-2,4-dimethoxychlorobenzene dihydrochloride | 0.723 g |
| p-Phenylenediamine | 0.27 g |
| ALFOL C 16/18 - company CONDEA (cetyl/stearyl alcohol) | 8 g |
| CIRE DE LANETTE E - company HENKEL (sodium cetyl/stearyl sulphate) | 0.5 g |
| CEMULSOL B - RHONE POULENC (ethoxylated castor oil) | 1 g |
| Oleic diethanolamine | 1.5 g |
| MASQUOL DTPA - company PROTEX (pentasodium salt of diethylenetriaminepentaacetic acid) | 2.5 g |
| Ammonia solution, 22° Be | 11 g |
| Sodium bisulphite solution, 35° Be | 1.3 g |
| Water qs | 100 g |
| pH: 9.7 | |

At the time of use, 100 g of "20 volumes" hydrogen peroxide are added. When applied for 20 minutes at 35° C. on hair which is naturally 90% white, the mixture imparts to the latter, after shampooing and rinsing, a dark purple-red colouration.

Application Example 4

The following dyeing mixture is prepared:

| | |
|---|---|
| 5-Amino-3-(β-hydroxyethyl)amino-2,4-dimethoxychlorobenzene dihydrochloride | 0.79 g |
| p-Phenylenediamine | 0.27 g |
| Oleyl alcohol polyglycerolated with 2 moles of glycerol | 4.5 g |
| Oleyl alcohol polyglycerolated with 4 moles of glycerol | 4.5 g |
| ETHOMEEN 0 12 - company ARMOON HESS CHEMICAL Ltd. (oleylamine oxyethylenated with 12 moles of EO) | 4.5 g |
| COMPERLAN KD - company HENKEL (coconut diethanolamide) | 9 g |
| Propylene glycol | 4 g |
| 2-Butoxyethanol | 8 g |
| Ethanol, 96° strength | 6 g |
| MASQUOL DTPA - company PROTEX (pentasodium salt of diethylenetriaminepentaacetic acid) | 2 g |
| Hydroquinone | 0.15 g |
| Sodium bisulphite solution, 35° Be | 1.3 g |
| Ammonia solution, 22° Be | 10 g |
| Water qs | 100 g |
| pH: 10 | |

At the time of use, 100 g of "20 volumes" hydrogen peroxide are added. When applied for 20 minutes at 30° C. on bleached hair, the mixture imparts to the latter, after shampooing and rinsing, a greyish brown colouration.

Application Example 5

The following dyeing mixture is prepared:

| | |
|---|---|
| 5-(β-Hydroxyethyl)amino-3-amino-2,4-dimethoxychlorobenzene dihydrochloride | 0.79 g |
| p-Phenylenediamine | 0.27 g |
| Oleyl alcohol polyglycerolated with 2 moles of glycerol | 4.5 g |
| Oleyl alcohol polyglycerolated with 4 moles of glycerol | 4.5 g |
| ETHOMEEN 0 12 - company ARMOON HESS CHEMICAL Ltd. (oleylamine oxyethylenated with 12 moles of EO) | 9 g |
| Propylene glycol | 4 g |
| 2-Butoxyethanol | 8 g |
| Ethanol, 96° strength | 6 g |
| MASQUOL DTPA - company PROTEX (pentasodium salt of diethylenetriaminepentaacetic acid) | 2 g |
| Hydroquinone | 0.15 g |
| Sodium bisulphite solution, 35° Be | 1.3 g |
| Ammonia solution, 22° Be | 10 g |
| Water qs | 100 g |
| pH: 10 | |

At the time of use, 100 g of "20 volumes" hydrogen peroxide are added. When applied for 25 minutes at 35° C. on natural grey hair, the mixture imparts to the latter, after shampooing and rinsing, a dark purple-red colouration.

Application Example 6

The following dyeing mixture is prepared:

| | |
|---|---|
| 5-(β-Hydroxyethyl)amino-3-amino-2,4-dimethoxychlorobenzene dihydrochloride | 1.11 g |
| 4-Amino-N—(β-methoxyethyl)aniline | 0.7 g |
| CEMULSOL NP 4 - RHONE POULENC (nonylphenol oxyethylenated with 4 moles EO) | 12 g |
| CEMULSOL NP 9 - RHONE POULENC (nonylphenol oxyethylenated with 9 moles EO) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |
| TRILON B (ethylenediaminetetraacetic acid) | 0.12 g |
| Ammonia solution, 22° Be | 11 g |
| Thioglycolic acid | 0.6 g |
| Water qs | 100 g |

| | |
|---|---|
| pH: 10.2 | |

At the time of use, 100 g of "20 volumes" hydrogen peroxide are added. When applied for 15 minutes at 35° C. on bleached hair, the mixture imparts to the latter, after shampooing and rinsing, a dark lilac colouration.

Application Example 7

The following dyeing mixture is prepared:

| | |
|---|---|
| 3,5-Bis(β-hydroxyethyl)amino-2,4-dimethoxychlorobenzene dihydrochloride | 1.09 g |
| 2,6-Dimethyl-para-phenylenediamine | 0.63 g |
| ALFOL C 16/18 - company CONDEA (cetyl/stearyl alcohol) | 19 g |
| EUTANOL G - company HENKEL (2-octyldodecanol) | 4.5 g |
| MERGITAL C.S. - company HENKEL (cetyl/stearyl alcohol with 15 moles EO) | 2.5 g |
| Ammonium lauryl sulphate | 10 g |
| Cationic polymer containing the following repeated unit: | |

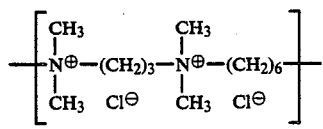

| | |
|---|---|
| of MW about 10,000 | |
| Benzyl alcohol | 2 g |
| Ammonia solution, 22° Be | 11 ml |
| TRILON B (ethylenediaminetetraacetic acid) | 1 g |
| Sodium bisulphite, 35° Be | 1.2 g |
| Water qs | 100 g |
| pH: 9.2 | |

At the time of use, 100 g of "20 volumes" hydrogen peroxide are added. When applied for 20 minutes at 30° C. on bleached hair, the mixture imparts to the latter, after shampooing and rinsing, a purple-blue colouration.

Application Example 8

The following dyeing mixture is prepared:

| | |
|---|---|
| 3,5-Diamino-2,4-dimethoxychlorobenzene dihydrochloride | 0.16 g |
| 5-Methylamino-3-amino-2,4-dimethoxychlorobenzene dihydrochloride | 0.20 g |
| p-Tolylenediamine dihydrochloride | 0.58 g |
| meta-Aminophenol | 0.26 g |
| Resorcinol | 0.16 g |
| CARBOPOL 934 - company GOODRICH CHEMICALS | 3 g |
| Alcohol, 96° strength | 11 g |
| 2-Butoxyethanol | 5 g |
| Trimethylcetylammonium bromide | 2 g |
| TRILON B (ethylenediaminetetraacetic acid) | 0.2 g |
| Ammonia solution, 22° Be | 10 g |
| Sodium bisulphite, 35° Be | 1 g |
| Water qs | 100 g |
| pH: 9.2 | |

At the time of use, 100 g of "20 volumes" hydrogen peroxide are added. When applied for 20 minutes at 35° C. on bleached hair, the mixture imparts to the latter, after shampooing and rinsing, a black colouration with red glints.

We claim:

1. Compounds corresponding to the formula

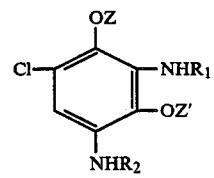

in which:

Z and Z' denote, independently of one another, an alkyl radical having from 1 to 4 carbon atoms or a hydroxyalkyl radical having from 2 to 4 carbon atoms, and $R_1$ and $R_2$ denote, independently of one another, a hydrogen atom, an alkyl radical having from 1 to 4 carbon atoms or a mono- or polyhydroxyalkyl radical having from 2 to 3 carbon atoms, with the proviso that, when $R_1$ and $R_2$ simultaneously denote a hydrogen atom, Z and Z' do not simultaneously denote a methyl radical, and acid addition salts.

2. The compound according to claim 1, which are selected from the group consisting of 3-(β-hydroxyethyl)amino-5-amino 2,4-dimethoxychlorobenzene, 3-amino-5-(β-hydroxyethyl)amino-2,4-dimethoxychlorobenzene, 3,5-bis(β-hydroxyethyl)amino-2,4-dimethoxychlorobenzene, 3-methylamino-5-amino-2,4-dimethoxychlorobenzene, 3,5-diamino-2,4-diethoxychlorobenzene and 3,5-diamino-2,4-bis(γ-hydroxypropoxy)chlorobenzene, and their addition salts with an inorganic acid.

3. A keratinous fiber dyeing composition comprising an aqueous mixture of at least one oxidation dye coupler of the formula (I) according to claim 1 or one of an acid addition salt thereof; and at least one oxidation dye developer compound of the para type.

4. The dyeing composition according to claim 3, an oxidation dye coupler compound selected from the group consisting of 5-(β-hydroxyethyl)amino-3-amino-2,4-dimethoxychlorobenzene, 5-amino-3-(β-hydroxyethyl)amino-2,4-dimethoxychlorobenzene, 3,5-bis(β-hydroxyethyl)amino-2,4-dimethoxychlorobenzene, 5-methylamino-3-amino-2,4-dimethoxychlorobenzene, 3,5-diamino-2,4-dimethoxychlorobenzene, 3,5-diamino-2,4-diethoxychlorobenzene and 3,5-diamino-2,4-bis(γ-hydroxypropoxy)chlorobenzene, and inorganic acid addition salts with an inorganic acid.

5. The dyeing composition according to claim 3 which contains 0.05 to 3.5% by weight of compound (I'), or of one of its addition salts with an acid, based on the total weight of the composition.

6. The dyeing composition according to claim 3, wherein the oxidation dye precursor of the para type is selected from the group consisting of para-phenylenediamines, para-aminophenols, heterocyclic para compounds and mixtures thereof.

7. The dyeing composition according to claim 6, wherein para-phenylenediamines correspond to the formula:

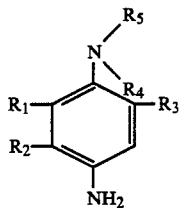

(VIII)

in which $R_1$, $R_2$ and $R_3$ are identical or different and denote a hydrogen or halogen atom, an alkyl radical having 1 to 4 carbon atoms or an alkoxy radical having 1 to 4 carbon atoms, and $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ having from 1 to 4 carbon atoms, or alternatively $R_4$ and $R_5$ can form, together with the nitrogen atom to which they are linked, a piperidino or morpholino heterocycle, with the proviso that $R_1$ or $R_3$ denotes a hydrogen atom when $R_4$ and $R_5$ do not denote a hydrogen atom, or are salts of compounds of the formula (VIII).

8. The dyeing composition according to claim 7, which contains at least one para-phenylenediamine chosen from the group consisting of p-phenylenediamine, isopropyl-p-phenylenediamine, p-tolylene-diamine, methoxy-para-phenylenediamine, chloro-para-phenylenediamine, 2,6-dimethyl-para-phenylenediamine, 2,3-dimethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-bis($\beta$-hydroxyethyl)-para-phenylenediamine, 3-methyl-4-amino-N,N-bis($\beta$-hydroxyethyl)aniline, 3-chloro-4-amino-N,N-bis($\beta$-hydroxyethyl)aniline, 4-amino-N-ethyl-N-(carbamylmethyl)aniline, 3-methyl-4-amino-N-ethyl-N-(carbamylmethyl)aniline, 4-amino-N-ethyl-N-($\beta$-piperidinoethyl)aniline, 3-methyl-4-amino-N-ethyl-N-($\beta$-piperidinoethyl)aniline, 4-amino-N-ethyl-N-($\beta$-morpholinoethyl)aniline, 3-methyl-4-amino-N-ethyl-N-($\beta$-morpholinoethyl)aniline, 4-amino-N-ethyl-N-($\beta$-acetylaminoethyl)aniline, 4-amino-N-($\beta$-methoxyethyl)aniline, 3-methyl-4-amino-N-ethyl-N-($\beta$-acetylaminoethyl)aniline, 4-amino-N-ethyl-N-($\beta$-mesylaminoethyl)aniline, 3-methyl-4-amino-N-ethyl-N-($\beta$-mesylaminoethyl)aniline, 4-amino-N-ethyl-N-($\beta$-sulphoethyl)aniline, 3-methyl-4-amino-N-ethyl-N-($\beta$-sulphoethyl)aniline, N-(4-aminophenyl)morpholine and N-(4-aminophenyl)piperidine, in the form of the free base or in the form of a cosmetically acceptable salt.

9. The dyeing composition according to claim 3, which contains at least one compound of the formula (I') in which $R_2$ is other than a hydrogen atom, or one of its salts with an acid, by way of a coupler, in combination with at least one para-phenylenediamine.

10. The dyeing composition according to claim 3, which contains at least one compound of formula (I') in which $R_2$ is a hydrogen atom, or one of its salts with an acid, by way of a coupler, in combination with at leat one para-phenylenediamine.

11. The dyeing composition according to claim 6, which contains at least one para-aminophenol selected from the group consisting of para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-($\beta$-hydroxyethyl)-4-aminophenol, 2-methoxy-4-aminophenol and 3-methoxy-4-aminophenol.

12. The dyeing composition according to claim 6, wherein the oxidation dye precursor of the para type is a heterocyclic para compound selected from the group consisting of 2,5-diaminopyridine, 2-hydroxy-5-aminopyridine and tetraaminopyrimidine.

13. The dyeing composition according to claim 3, which contains other couplers selected from the group consisting of meta-diphenols, meta-aminophenols, meta-phenylenediamines, meta-acylaminophenols, meta-ureidophenols, meta-carbalkoxyaminophenols, $\alpha$-naphthol, $\beta$-keto compounds and pyrazolones.

14. The dyeing composition according to claim 3, wherein the total concentration with respect to oxidation dye precursors of the para type and couplers is between 0.1 and 7% by weight.

15. The dyeing composition according to claim 3, which contains, in addition, dye precursors of the ortho type, selected from the group consisting of orthoaminophenols, ortho-phenylenediamines and ortho-diphenols.

16. The dyeing composition according to claim 3 which contains, in addition, direct dyes chosen from azo and anthraquinone dyes and nitro derivatives of the benzene series.

17. The dyeing composition according to claim 3, which has a pH of between 8 and preferably between 9 and 11.

18. The dyeing composition according to claim 3, which contains 1 to 40% by weight of an organic solvent chosen from the group consisting of lower alkanols, glycerol, glycols, glycol ethers, and mixtures thereof.

19. The dyeing composition according to claim 3, which contains, in addition, 0.5 to 40% by weight of at least one anionic, cationic, nonionic or amphoteric surfactant, or mixtures thereof.

20. The dyeing composition according to claim 3, which contains, in addition, cosmetic adjuvants chosen from the group consisting of thickeners, antioxidant agents, penetrating agents, sequestering agents, buffers, perfumes, alkanalizing agents and propellants.

21. A process for dyeing keratinous fibers comprising contacting said keratinous fibers with a dyeing composition according to the claim 3.

22. A process for dyeing hair comprising in sequence the steps of
(a) mixing at least one oxidation dye coupler of the formula I' according to claim 1 or an acid addition salt thereof; and at least one oxidation dye developer compound of the para type;
(b) applying to the hair the resulting composition from step (a);
(c) permitting said compositions from step (a) to remain in contact with the hair for a period ranging from 10 to 40 minutes to form a dye on the hair; then
(d) rinsing,
(e) shampooing, and
(f) drying the dyed hair.

23. A process for dyeing hair comprising in sequence the steps of:

(a) applying to the hair a dyeing composition containing at least one oxidation dye precursor of the para type;
(b) applying to the hair at least one dyeing composition of the formula (I) or an acid salt thereof and an oxidizing agent;
(c) permitting said compositions from step (a) and step (b) remain in contact with the hair for a period ranging from 10 to 40 minutes to form a dye on the hair, then
(d) rinsing,
(e) shampooing and
(f) drying the dyed hair.

* * * * *